United States Patent [19]

Lilley

[11] Patent Number: 5,158,456

[45] Date of Patent: Oct. 27, 1992

[54] TURBINE AIR EXHAUST BLOCK

[76] Inventor: Hal D. Lilley, P.O. Box 141, Corry, Pa. 16407

[21] Appl. No.: 649,954

[22] Filed: Feb. 4, 1991

[51] Int. Cl.$^5$ .............................................. A61C 1/16
[52] U.S. Cl. .................................................... 433/116
[58] Field of Search .................. 433/115, 116, 82, 84, 433/85, 229

[56] References Cited

U.S. PATENT DOCUMENTS

| | | | |
|---|---|---|---|
| 684,951 | 10/1901 | Rothkranz | 433/116 |
| 1,101,947 | 6/1914 | Morgan | 433/116 X |
| 1,476,976 | 12/1923 | Ivory | 433/116 X |
| 1,549,165 | 8/1925 | Thiedemann | 433/116 |
| 1,821,451 | 9/1931 | Terry | 433/116 |
| 2,731,722 | 1/1956 | Wilen | 433/116 X |
| 2,835,084 | 5/1958 | Fotre | 433/116 X |
| 2,855,672 | 10/1958 | Franwick et al. | 433/84 |
| 3,815,241 | 6/1974 | Lingenhohle et al. | 433/115 X |
| 4,752,223 | 6/1988 | Carlson | 433/116 |

Primary Examiner—Gene Mancene
Assistant Examiner—Nicholas D. Lucchesi

[57] ABSTRACT

An attachment for a dental handpiece comprised of a circular band with an extended channel and slot on opposite sides, fitted with a pliable material insert, which can be mounted to a dental handpiece. The main purpose of the Handpiece Turbine Air Exhaust Block is to effectively block the air and water coolant ports with its pliable material insert. Blocking the air coolant port is desired when operating the handpiece near open wounds in the mouth, in order to avoid air emphysema. Further, blocking the water pot eliminates the problem of "suck back", a condition where a handpiece will harbor infectious diseases and transmit them to the next patient.

1 Claim, 1 Drawing Sheet

TURBINE AIR EXHAUST BLOCK

FIELD OF THE INVENTION

This invention relates to dental handpieces, and more particularly to a circular band device with pliable assembly to be used as a disposable unit on dental handpieces.

BACKGROUND OF THE INVENTION

The use of high-speed air-cooled rotary cutting instruments is common in dental practices. When used near open wounds, the forced air can lead to subcutaneous emphysema and involvement of vital structures.

There are dental handpieces on the market that are driven by means other than an air turbine, but they are very expensive in comparison to the average turbine handpiece, and are therefore not as widely used. Because of the expense of the non-air driven handpieces, most dentists continue to use the air-driven models on their patients for third molar extractions where open wounds occur. This problem is solved by the use of a device built specifically to block the air and water coolant parts during these types of operations.

Applicant has reviewed the patent documents of U.S. Pat. Nos. 1,476,976—Ivory, 4,752,223—Carlson, 2,731,722—Wilen, 2,835,084—Fotre, 1,549,165—Theidemann, 684,951—Rothkranz, 1,101,947—Morgan, 2,855,672—Franwick et al, 3,815,241—Lingenhohle et al, 1,821,451—Terry, and has found all of them to be for dental handpiece accessories, but none are related to the blocking of the air and water ports of the handpiece.

SUMMARY OF THE INVENTION

The Handpiece Turbine Air Exhaust Block is an accessory for a high speed dental handpiece that blocks the air and water coolant ports.

DETAILED DESCRIPTION

Figure 1:
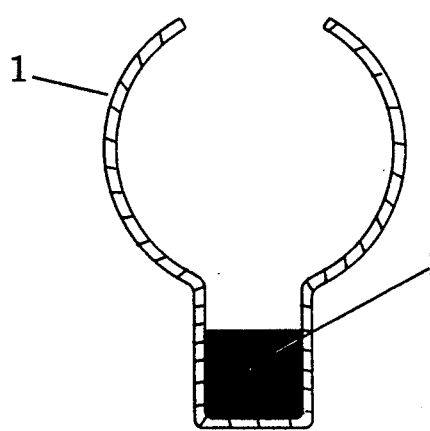
FIG. 1 is an end view of the circular band device with pliable material insert.
Figure 2:
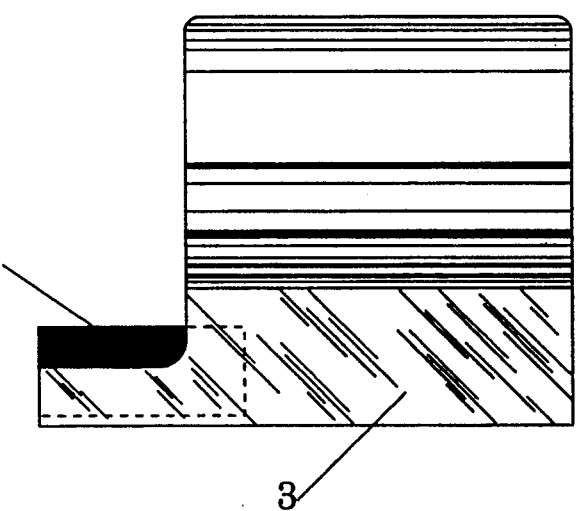
FIG. 2 is a side view of FIG. 1 where a piece of pliable material is located in the extended channel of the circular band device.

The Handpiece Turbine Air Exhaust Block is a circular band 1 that has been formed so that it will snap securely on to a round shaft which is the approximate size of the shaft nearest the turbine head that embodies the air and water coolant ports on most dental handpieces. The Handpiece Turbine Air Exhaust Block is fitted with a small piece of pliable material 2 at one end of the extended channel 3 that will cover the coolant ports on a dental handpiece.

I claim:

1. In combination with a dental handpiece having an extended shaft and at least one fluid opening adjacent to a head portion of the handpiece, a removable circular band having a longitudinal axis, attached to the shaft of the handpiece, the band having an expansion slot running parallel to said axis, a channel attached to and extending from the band in a direction parallel to said axis, the channel having a section of pliable material therein, the pliable material covering the said at least one opening of the handpiece.

* * * * *